United States Patent

Mao et al.

[11] Patent Number: 5,891,592
[45] Date of Patent: Apr. 6, 1999

[54] ADDITIVES FOR IMPROVING CYCLE LIFE OF NON-AQUEOUS RECHARGEABLE LITHIUM BATTERIES

[75] Inventors: Huanyu Mao, Burnaby; Ulrich Von Sacken, Coquitlam; Jan Naess Reimers, Maple Ridge, all of Canada

[73] Assignee: NEC Moli Energy (Canada) Limited, Maple Ridge, Canada

[21] Appl. No.: 811,585

[22] Filed: Mar. 5, 1997

[30] Foreign Application Priority Data

Jan. 31, 1997 [CA] Canada ................................ 2196493

[51] Int. Cl.⁶ ........................................ H01M 6/16
[52] U.S. Cl. ............................... 429/197; 429/194
[58] Field of Search ........................ 429/194, 197, 429/198

[56] References Cited

FOREIGN PATENT DOCUMENTS

| | | |
|---|---|---|
| 2150877 | 6/1995 | Canada . |
| 2175755 | 5/1996 | Canada . |
| 705848 | 4/1996 | European Pat. Off. . |
| 6-263866 | 9/1994 | Japan . |
| 7-105955 | 4/1995 | Japan . |
| 7-142055 | 6/1996 | Japan . |
| WO 9615080 | 5/1996 | WIPO . |
| WO 97/16862 | 5/1997 | WIPO . |

OTHER PUBLICATIONS

S.S. Zhang and C.A. Angell, A Novel Electrolyte Solvent for Rechargeable Lithium and Lithium–Ion Batteries, J. Electrochem. Soc., vol. 143, No. 12, Dec. 1996, pp. 4047–4053.
CA: 124:330270 Solid Electroytic capacitors, (1998).

*Primary Examiner*—Maria Nuzzolillo
*Assistant Examiner*—Voneil Parchment
*Attorney, Agent, or Firm*—Synnestvedt & Lechner

[57] ABSTRACT

The loss in delivered capacity (fade) after cycling non-aqueous rechargeable lithium batteries can be reduced by incorporating a small amount of certain additive compounds in the battery. The additive compound comprises boron, oxygen, and organic end groups that are chemically compatible with the battery components. The structure of the additive compound contains a boroxine $(BO)_3$ ring. The invention is particularly suited to lithium ion batteries. Trimethoxyboroxine and trimethylboroxin are particularly effective additives. Preferably, the additive compound is dissolved in the electrolyte.

25 Claims, 5 Drawing Sheets

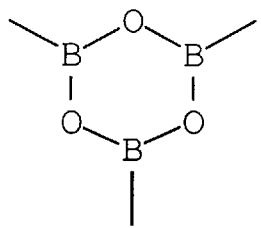
Fig. 2a - boroxine ring
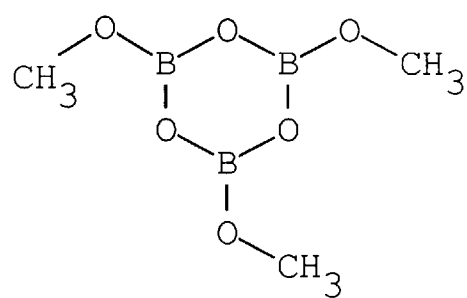
Fig. 2b - trimethoxyboroxine
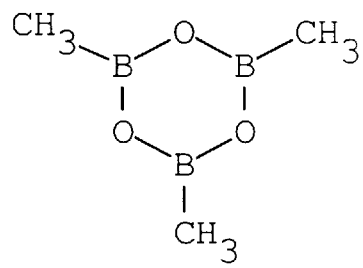
Fig. 2c - trimethylboroxin

ADDITIVES FOR IMPROVING CYCLE LIFE OF NON-AQUEOUS RECHARGEABLE LITHIUM BATTERIES

FIELD OF THE INVENTION

This invention pertains to non-aqueous rechargeable lithium batteries and to methods for improving the performance thereof. Specifically, it pertains to the use of compounds containing a boroxine $(BO)_3$ ring as an electrolyte additive as means for improving the capacity delivered from lithium ion batteries after extended cycling.

BACKGROUND OF THE INVENTION

Many types of non-aqueous rechargeable lithium batteries are used commercially for consumer electronics applications. Typically, these batteries employ a lithium insertion compound as the active cathode material, a lithium compound of some sort (eg. pure lithium metal, lithium alloy, or the like) as the active anode material, and a non-aqueous electrolyte. An insertion compound is a material that can act as a host solid for the reversible insertion of guest atoms (in this case, lithium atoms).

Lithium ion batteries use two different insertion compounds for the active cathode and anode materials. Currently available lithium ion batteries are high voltage systems based on $LiCoO_2$ cathode and coke or graphite anode electrochemistries. However, many other lithium transition metal oxide compounds are suitable for use as the cathode material, including $LiNiO_2$ and $LiMn_2O_4$. Also, a wide range of carbonaceous compounds is suitable for use as the anode material. These batteries employ non-aqueous electrolytes comprising $LiBF_4$ or $LiPF_6$ salts and solvent mixtures of ethylene carbonate, propylene carbonate, diethyl carbonate, and the like. Again, numerous options for the choice of salts and/or solvents in such batteries are known to exist in the art.

The excellent reversibility of this insertion combination makes it possible for lithium ion batteries to achieve hundreds of battery cycles. However, a gradual loss of lithium and/or buildup of impedance can still occur upon extended cycling for various reasons. This in turn typically results in a gradual loss in delivered capacity with increasing cycle number. Researchers in the art have devoted substantial effort to reducing this loss in capacity. For instance, co-pending Canadian patent application serial number 2,150,877, filed Jun. 2, 1995, and titled "Use of $P_2O_5$ in Non-aqueous Rechargeable Lithium Batteries" discloses a means for reducing this loss which involves exposing the electrolyte to $P_2O_5$. However, $P_2O_5$ shows at best only limited solubility in typical non-aqueous electrolytes and can be somewhat awkward to use in practice. Alternatives which are soluble may be more convenient, but it is unclear why such $P_2O_5$ exposure is effective and hence what compounds might serve as effective alternatives.

$B_2O_3$ is a common chemical that is extensively used in the glass industry, and its properties are well known. $B_2O_3$ has also been used in the lithium battery industry for a variety of reasons. In most cases, the $B_2O_3$ is used as a precursor or reactant to prepare some other battery component. However, Japanese published patent application 07-142055 discloses that lithium batteries can show improved stability to high temperature storage when using lithium transition metal oxide cathodes which contain $B_2O_3$. Also, co-pending Canadian patent application serial number 2,175,755, filed May 3, 1996, and titled "Use of $B_2O_3$ additive in Non-aqueous Rechargeable Lithium Batteries" discloses that $B_2O_3$ additives can be used to reduce the rate of capacity loss with cycling in rechargeable lithium batteries and that this advantage can be obtained by having the additive dissolved in the electrolyte. However, the reason that the $B_2O_3$ additive resulted in an improvement with cycling was not understood.

$B_2O_3$ commonly exists in a vitreous or glassy state. The structure is complex and is believed to consist of sheets of randomly oriented, 6 membered $(BO)_3$ boroxine rings which are connected by additional bridging oxygen atoms. (Crystalline $B_2O_3$ can be obtained, but only with significant difficulty. Crystalline $B_2O_3$ also has a complicated structure consisting of linked sets of zig-zag chains which form a three dimensional network structure.)

Certain other compounds containing boron, oxygen, carbon, and hydrogen (eg. trimethoxyboroxine, trimethylboroxin, trimethyl borate, tri-tert-butyl borate) have been used in the preparation of other compounds, particularly polymers. For instance, trimethoxyboroxine has been used to promote cross linking of silanes for Si-Si bond formation (PCT International Patent Application Serial No. WO9615080), as a catalyst for producing olefin polymers (European Patent Application EP705848), and to improve the melt stability of high molecular weight polycarbonates (Japanese laid-open patent application JP 06263866).

In battery and/or fuel cell applications, compounds containing boron, oxygen, carbon, and hydrogen such as trimethyl borate have been used as a precursor in a process to make an electrode substrate. For instance, in Japanese laid-open patent application JP 07105955, a precursor B-containing compound was kneaded in with the other electrode components before heat treating the mixture to 1000 degrees C. Boron-oxygen-carbon-hydrogen containing compounds have also been used in the preparation of lithium haloboracite (lithium-boron-oxygen-halogen containing material) solid electrolyte films for battery usage. However, it appears that these compounds have not heretofore been used directly in lithium batteries as additives or for any other purpose.

SUMMARY OF THE INVENTION

Rechargeable batteries exhibit a loss in delivered capacity as a function of the number of charge/discharge cycles. Herein, the fractional loss of capacity per cycle is referred to as the capacity fade rate. The instant invention comprises non-aqueous rechargeable lithium batteries having improved fade rates and methods for achieving the reduced fade rate. Non-aqueous rechargeable lithium batteries generally comprise a lithium insertion compound cathode, a lithium compound anode, and a nonaqueous electrolyte comprising a lithium salt dissolved in a non-aqueous solvent. Incorporating a small amount of certain compounds in the batteries can result in improved fade rate characteristics. Preferably, the compounds are dissolved in the electrolyte. Such compounds therefore serve to function as fade rate reducing additive compounds.

The fade rate reducing additive compounds comprise boron, oxygen, and organic end groups wherein the end groups are chemically compatible with the other battery components. The additive compounds can have structures ranging from the simple to the complex. However, the fade reducing additive compounds share a chemically similar structure comprising at least one 6 member boroxine $(BO)_3$ ring. The additive compounds therefore show certain chemical similarities to glassy $B_2O_3$ in that the framework of each molecule comprises $(BO)_3$ rings and perhaps other interconnecting B—O bonds.

The organic end groups of the additive are, by definition, relatively inert with respect to the components and function of the non-aqueous rechargeable lithium battery. Aliphatic hydrocarbons are generally inert to lithium metal and other lithium battery components. Thus, the organic end groups can be aliphatic hydrocarbons. However, many other organic compounds are also relatively inert with respect to lithium battery components. For instance, the solvents which are commonly employed in conventional lithium batteries are relatively inert. (Reaction with lithium may occur to some extent but may be limited by the formation of a passivation layer.) Thus, it is expected that the organic end groups can be derived from certain solvents from groups such as linear or cyclic carbonates, ethers, lactones, and the like.

The fade rate reducing additive compound can therefore have the structure denoted

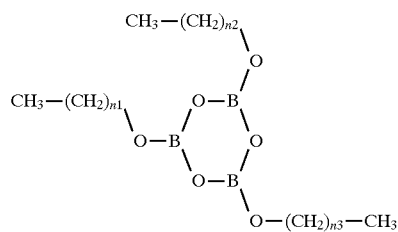

wherein $n_1$, $n_2$, and $n_3$ are integers greater than or equal to zero. In particular, $n_1$, $n_2$, and $n_3$ can be 0, thereby corresponding to the compound trimethoxyboroxine.

Alternately, the fade rate reducing additive compound can have the structure denoted

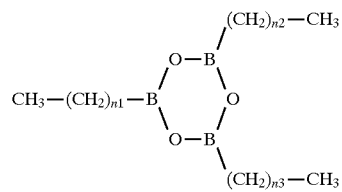

wherein $n_1$, $n_2$, and $n_3$ are integers greater than or equal to zero. In particular, $n_1$, $n_2$, and $n_3$ can be 0, thereby corresponding to the compound trimethylboroxin.

Reduced fade rates can be achieved for batteries employing conventional lithium ion battery electrochemistries. Thus, the cathode can be a lithium transition metal oxide, in particular the layered compound $LiCoO_2$ or the spinel $LiMn_2O_4$. The anode can be a carbonaceous insertion compound anode, in particular graphite. The electrolyte can contain $LiPF_6$ salt dissolved in an organic carbonate solvent, in particular mixtures containing ethylene carbonate, propylene carbonate, ethyl methyl carbonate, and/or diethyl carbonate solvents.

In principle, the fade rate reducing additive compounds can be incorporated as a solid in the battery. However, the additives are preferably dispersed inside the battery. Also, the additives may be hygroscopic which makes it more difficult to deal with these compounds during battery manufacture. For these reasons, the additive compounds are preferably dissolved in the electrolyte. The aforementioned fade rate reducing additive compounds can be liquid at ambient temperature (eg. trimethoxyboroxine and trimethylboroxin). This feature can be advantageous since a liquid can be easier and faster to dissolve in the battery electrolyte than a solid, such as $B_2O_3$.

Conventional assembly methods can be used to prepare a battery of the invention, except that an additional step is required wherein an amount of one of the aforementioned fade rate reducing additive compounds is incorporated in the battery as well. A preferred method for accomplishing this is simply to dissolve a suitable amount of additive compound into the electrolyte solvent prior to using the electrolyte during assembly of the battery.

Incorporating an amount of fade rate reducing additive in the range from greater than about 0.5% of the weight of the electrolyte can be effective in improving capacity fade rate. Preferably, however, a sufficiently small amount of fade rate reducing additive is incorporated in the electrolyte such that other desirable bulk properties of the battery are not adversely affected, eg. such that the thermal stability threshold of the battery remains essentially unchanged. In this way, other bulk properties such as the relative safety of the battery are not compromised by the inclusion of the additive. For certain choices of fade rate reducing additive compounds, incorporated amounts ranging from about 0.5% to less than about 2% of the weight of the electrolyte can be effective in improving capacity fade rate without compromising fundamental battery safety.

BRIEF DESCRIPTION OF THE DRAWINGS

In drawings which illustrate specific embodiments of the invention, but which should not be construed as restricting the spirit or scope of the invention in any way:

FIG. 2 shows the chemical structure of a $(BO)_3$ boroxine ring, and two fade reducing additive compounds of the invention: trimethoxyboroxine and trimethylboroxin.

DETAILED DESCRIPTION OF SPECIFIC EMBODIMENTS OF THE INVENTION

Figure 1:
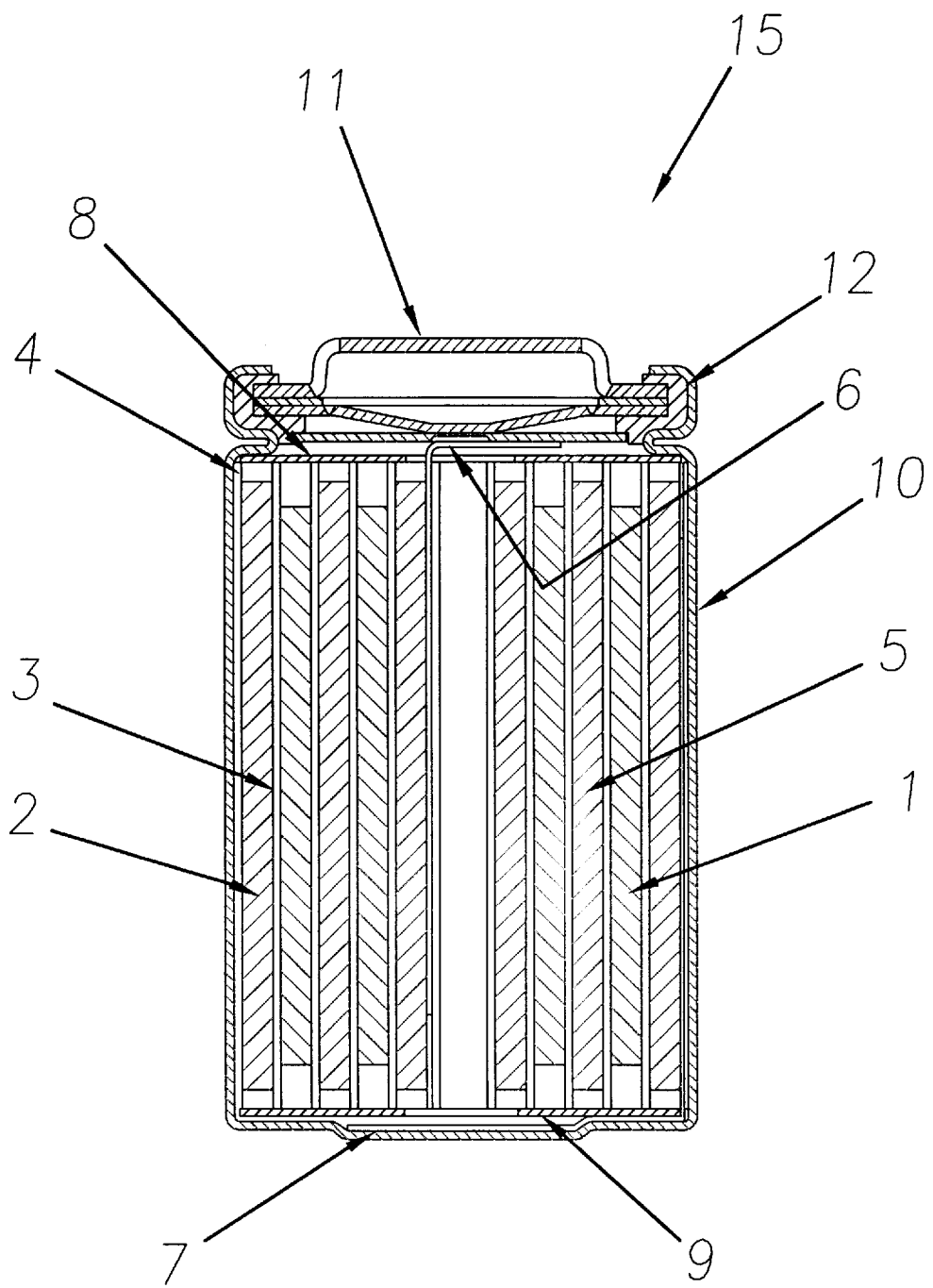
FIG. 1 depicts a cross-sectional view of a preferred embodiment of a cylindrical spiral-wound lithium ion battery.

Co-pending Canadian patent application serial number 2,175,755, filed May 3, 1996, teaches that the capacity fade rate characteristic of non-aqueous lithium rechargeable batteries in general can be improved by dissolving a small amount of $B_2O_3$ additive in the electrolyte. However, the reasons for this improvement were unclear. Thus, it was not known what features of $B_2O_3$ were important chemically for purposes of observing a fade rate improvement.

We have discovered that fade rate improvement can also be achieved using certain other additive compounds consisting of boron, oxygen, and organic end groups. These compounds comprise at least one $(BO)_3$ boroxine ring in their structure. There may be open chain portions consisting of oxygen and/or boron atoms connected to the boroxine ring. Additionally, there can be more than one boroxine ring in the structure in principle. Thus, the boron-oxygen bonding arrangement of the additive compounds shows similarities to that of glassy $B_2O_3$. The organic end groups are chemically compatible with the battery components. In other words, the end groups are relatively inert with respect to the cathode, anode, and electrolyte and therefore should not interfere with the normal functioning of the battery. The more common end groups are aliphatic hydrocarbons. Such hydrocarbons (eg. pentane, cyclohexane) are generally inert and do not react with the other battery components during normal battery operation. Preferred examples of suitable additive compounds are trimethoxyboroxine and trimethylboroxin, both having the advantage of being relatively small molecules and liquids at ambient temperature. While fade rate improvement can be achieved, some tradeoffs in other battery characteristics may occur with the use of such additives. Thus, a balance must be struck between these characteristics when selecting the amount of additive to use.

Typically, this type of battery employs a lithium insertion compound as the cathode and one of a variety of lithium compounds as the anode. Possible lithium compounds include lithium metal, lithium alloys, and lithium insertion compounds. Preferred embodiments are lithium ion batteries wherein the anode is also a lithium insertion compound. Presently, the majority of commercial lithium ion batteries employ transition metal oxide cathodes (either $LiCoO_2$, $LiNiO_2$, or $LiMn_2O_4$) and carbonaceous anodes (either coke or graphite).

Preferred electrolytes for lithium ion batteries comprise $LiPF_6$ salt dissolved in a mixture of non-aqueous organic carbonate solvents (such as ethylene carbonate, propylene carbonate, ethyl methyl carbonate, and/or diethyl carbonate). This choice of salts can result in a safer, more stable, electrolyte than would some other salt choices.

If only a small amount (circa 1% by weight of that of the electrolyte) of additive compound is incorporated in the battery, the other bulk characteristics of the electrolyte can remain largely unaffected. In principle, the additive may be incorporated in solid form. Preferably however, the additive is dissolved in the electrolyte. As a result, the additive is well dispersed throughout the battery. Also, it can make it easier to handle the additive during manufacture if the additive is hygroscopic or difficult to incorporate into either electrode for some reason.

It should be noted that the presence of additive compound can result in an increase in the irreversible capacity loss experienced during the first charging of such batteries. Also, the use of too much additive compound can adversely affect the thermal stability threshold of such batteries. And, an excessive amount of dissolved additive compound could be expected to adversely affect electrolyte conductivity and hence battery rate capability. Thus, it is important not only to determine the capacity fade rate as a function of amount of additive in any particular embodiment, but also to determine the effects of amount of additive on these other important battery characteristics. Some non-inventive characterization trials must thus be performed in order to arrive at a sensible tradeoff between fade rate improvement and these other characteristics.

The invention relates to battery constructions with one of the aforementioned additive compounds dissolved in the electrolyte. Various battery configurations are suitable, including prismatic formats or miniature coin cells. A preferred conventional construction for a lithium ion type product is depicted in the cross-sectional view of a spiral-wound battery in FIG. 1. A jelly roll 4 is created by spirally winding a cathode foil 1, an anode foil 2, and two microporous polyolefin sheets 3 that act as separators.

Cathode foils are prepared by applying a mixture of a suitable powdered (about 10 micron size typically) cathode material, such as a lithiated transition metal oxide, possibly other powdered cathode material if desired, a binder, and a conductive dilutant onto a thin aluminum foil. Typically, the application method first involves dissolving the binder in a suitable liquid carrier. Then, a slurry is prepared using this solution plus the other powdered solid components. The slurry is then coated uniformly onto the substrate foil. Afterwards, the carrier solvent is evaporated away. Often, both sides of the aluminum foil substrate are coated in this manner and subsequently the cathode foil is calendered.

Anode foils are prepared in a like manner except that a powdered (also typically about 10 micron size) carbonaceous insertion compound is used instead of the cathode material and thin copper foil is usually used instead of aluminum. Anode foils are typically slightly wider than the cathode foils in order to ensure that anode foil is always opposite cathode foil.

The jelly roll 4 is inserted into a conventional battery can 10. A header 11 and gasket 12 are used to seal the battery 15. The header may include safety devices if desired such as a combination safety vent and pressure operated disconnect device. Additionally, a positive thermal coefficient device (PTC) may be incorporated into the header to limit the short circuit current capability of the battery. The external surface of the header 11 is used as the positive terminal, while the external surface of the can 10 serves as the negative terminal.

Appropriate cathode tab 6 and anode tab 7 connections are made to connect the internal electrodes to the external terminals. Appropriate insulating pieces 8 and 9 may be inserted to prevent the possibility of internal shorting.

Lithium ion batteries of the invention have a fade rate reducing additive compound incorporated therein in order to improve the fade rate. Preferably, the additive is dissolved in the electrolyte which can be accomplished in a variety of ways. However, the most straightforward and thus the preferred method simply involves dissolving a suitable amount of a liquid additive compound in the electrolyte solvent before filling the battery with the electrolyte. Then, prior to crimping the header 11 to the can 10 and sealing the battery, the electrolyte 5 comprising the fade rate reducing additive is added to fill the porous spaces in the jelly roll 4.

At this point, the battery is in a fully discharged state. Generally, an electrical conditioning step, involving at least a single complete recharge of the battery, is performed as part of the overall assembly. One of the reasons for so doing is that some initial irreversible processes take place on this first recharge. For instance, a small amount of lithium is irreversibly lost during the first lithiation of the carbonaceous anode.

Advantages of the invention can be achieved using modest amounts of fade rate reducing additive compound. In the examples to follow, desirable results were obtained using of order of 1% additive by weight in the electrolyte. As mentioned above, some tradeoffs in other desirable battery characteristics can be expected if excessive amounts of additive compound are employed. For instance, care must be taken not to unacceptably alter the thermal stability threshold of the battery by using the additive. Also, care must be taken not to unacceptably increase the irreversible capacity loss experienced in lithium ion batteries by using the additive. Some straightforward quantification trials usually would be required in order to select an appropriate amount of additive compound to use.

At this time, the reason for the fade rate improvement using such additive compounds is unclear. Without being adversely bound by theory, a possible explanation is that the presence of these additive compounds in the electrolyte affects the passivation/decomposition reactions which occur at the anode surface in lithium batteries. It is possible that a passivation film is initially formed as a result of these reactions which inhibits the further decomposition of electrolyte at the anode. Further decomposition not only consumes some active lithium, but also results in the formation of decomposition products which, in turn, may coat the electrode material or otherwise adversely impede ionic transport thereby resulting in an increase in battery impedance (and hence result in a loss of deliverable capacity at a given rate). The presence of the additive compounds may result in the production of a chemically different passivation film and/or affect the rate of further decomposition reactions. Therefore, the benefits of the invention might be expected when using additive compounds which are chemically similar to glassy $B_2O_3$ or to those used in the Examples below.

The following Examples are provided to illustrate certain aspects of the invention but should not be construed as limiting in any way. 18650 size cylindrical batteries (18 mm diameter, 650 mm height) were fabricated as described in the preceding and shown generally in FIG. 1. Cathodes 1 comprised a mixture of transition metal oxide powder, a carbonaceous conductive dilutant, and polyvinylidene fluoride (PVDF) binder that was uniformly coated on both sides of a thin aluminum foil. The transition metal oxides used were either $LiCoO_2$ or $Li_{1.11}Mn_2O_4$ as indicated below. (Note that the ratio 1.11:1 for the starting Li:Mn stoichiometry is preferred for cycle life purposes.) Anodes 2 were made using a mixture of a spherical graphitic powder plus SUPER S™ (trademark of Ensagri) carbon black and PVDF binder that was uniformly coated on thin copper foil. Setela ® microporous polyethylene film was used as the separators 3.

The electrolytes 5 employed were solutions of 1M $LiPF_6$ salt dissolved in either a solvent mixture of ethylene carbonate (EC), propylene carbonate (PC), diethyl carbonate (DEC) solvents in a volume ratio of 30/20/50 respectively, or a solvent mixture of ethylene carbonate (EC), propylene carbonate (PC), ethyl methyl carbonate (EMC) solvents in a volume ratio of 30/10/60 respectively. The former will henceforth be referred to as the EC/PC/DEC electrolyte and the latter as the EC/PC/EMC electrolyte. The choice of $LiPF_6$ salt can result in a safer, more stable electrolyte than would other salt choices.

To protect against hazardous conditions on overcharge of the battery, the header of these batteries included a pressure operated electrical disconnect device. The electrolytes employed also contained 2.5% biphenyl additive by weight to act as a gassing agent for purposes of activating the electrical disconnect device (in accordance with the disclosure in co-pending Canadian Patent Application Serial No. 2,163,187, filed Nov. 17, 1995, titled "Aromatic Monomer Gassing Agents for Protecting Non-aqueous Lithium Batteries Against Overcharge", by the same applicant). Finally, the electrolytes 5 employed also contained certain fade reducing additive compounds in amounts ranging from about 0.1 to 2.0% by weight. Approximately 4 cc of electrolyte was used in each battery.

For electrical testing, batteries were thermostatted at 21 ±1° C. Cycling was performed using a current limited (1A maximum), constant voltage charge (4.1 volts for $LiCoO_2$ based batteries and 4.2 volts for $LiMn_2O_4$ based batteries) for 2.5 hours and a constant current discharge (1.5 amp for $LiCoO_2$ based batteries and 1 amp for $LiMn_2O_4$ based batteries) to a 2.5 volt cutoff. (Note: For purposes of observing changes in battery impedance, a prolonged, low rate charging or discharging was performed every 20 cycles. Subsequent discharge capacities may then be significantly different from than the previous ones. Many of these points have been omitted from the data presented below for purposes of clarity. However, this type of testing can introduce a noticeable discontinuity in the capacity versus cycle number data curves.

Examples with $LiCoO_2$ cathode and trimethoxyboroxine additive

Figure 3:
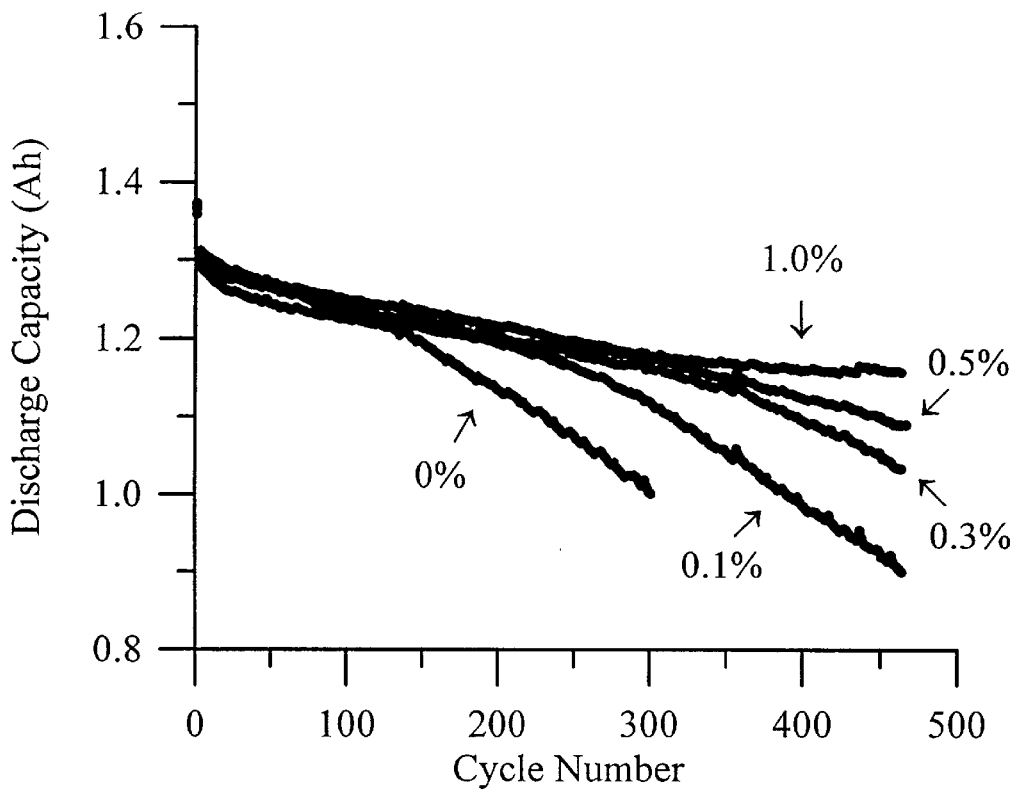
FIG. 3 shows the capacity versus cycle number data for the series of $LiCoO_2$ cathode based 18650 size batteries comprising 0%, 0.1%, 0.3%, 0.5%, and 1% wt. trimethoxyboroxine additive in the electrolyte.

A series of $LiCoO_2$ cathode based 18650 batteries was constructed with varying amounts of the fade reducing additive trimethoxyboroxine dissolved in the EC/PC/DEC electrolyte prior to assembly. The amounts employed were 0% (control), 0.1%, 0.3%, 0.5%, and 1% by weight in the electrolyte. The batteries were then cycled as described above. FIG. 3 shows the capacity versus cycle number data for each battery. The capacity fade rate is seen to progressively improve with an increasing amount of additive. (Note however that a very small increase in the irreversible loss of lithium during the first conditioning charge is evident with increasing amount of additive. Thus the capacity of batteries with more additive is slightly less than that of the control over the first few cycles.)

Figure 4:
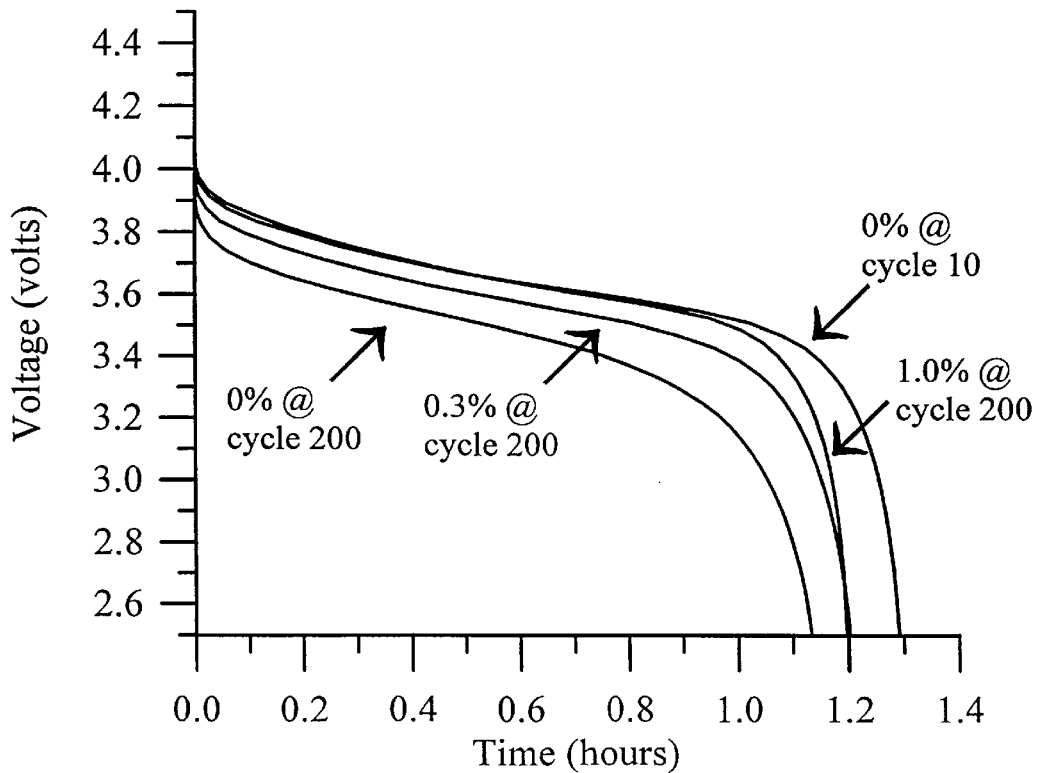
FIG. 4 shows the discharge voltage profiles for cycle numbers 10 and 200 for the control battery with 0% wt. additive and cycle number 200 for the batteries with 0.3% wt. and 1% wt. additive in the series of $LiCoO_2$ cathode based 18650 size batteries with trimethoxyboroxine additive.

FIG. 4 shows the voltage profiles of discharge number 10 and 200 for the control battery with 0% wt. additive and discharge number 200 for the battery with 0.3% and 1% wt. additive. The voltage profiles indicate a significant increase in battery impedance has occurred in the control battery with cycling. However, the impedance increase is progressively reduced with increasing amount of additive.

As shown in co-pending Canadian patent application serial number 2,175,755, the use of a $B_2O_3$ additive can adversely affect the thermal threshold stability of such batteries. Consequently, it may be important not to use an excessive amount of additive. To determine what amount might be excessive in this regard, four additional 18650 batteries were constructed as above using the larger amounts of trimethoxyboroxine. Thus, two sets of two batteries were made comprising 1% and 2% trimethoxyboroxine additive by weight in the electrolyte respectively. The batteries were electrically conditioned, charged to 4.1 V, and then exposed to a temperature of 150° C. in a convection oven (a "hot box" thermal stability test). Since the batteries were not heat sink to the oven, exothermic chemical reactions can be triggered within the batteries which, in turn, can result in further heating and potential thermal run away. The thermal response of each battery was monitored.

In this "hot box" test, the safety vent of conventional 18650 batteries (ie. without any additive) is normally activated due to pressure buildup. Normally, no fire nor violent venting is observed. Thermal run away is thus normally avoided. For the two batteries comprising 1% wt. trimethoxyboroxine additive, the safety vent activated but there was no fire nor violent venting. However, for the two batteries comprising 2% wt. trimethoxyboroxine additive, the safety vent activated and both batteries burned with a significant flame. One of these batteries additionally ejected its header with considerable force. Thus, a 2% wt. level of trimethoxyboroxine additive seemed to adversely affect the thermal threshold stability of these particular batteries.

Examples with LiCoO$_2$ cathode and trimethylboroxin additive

Figure 5:
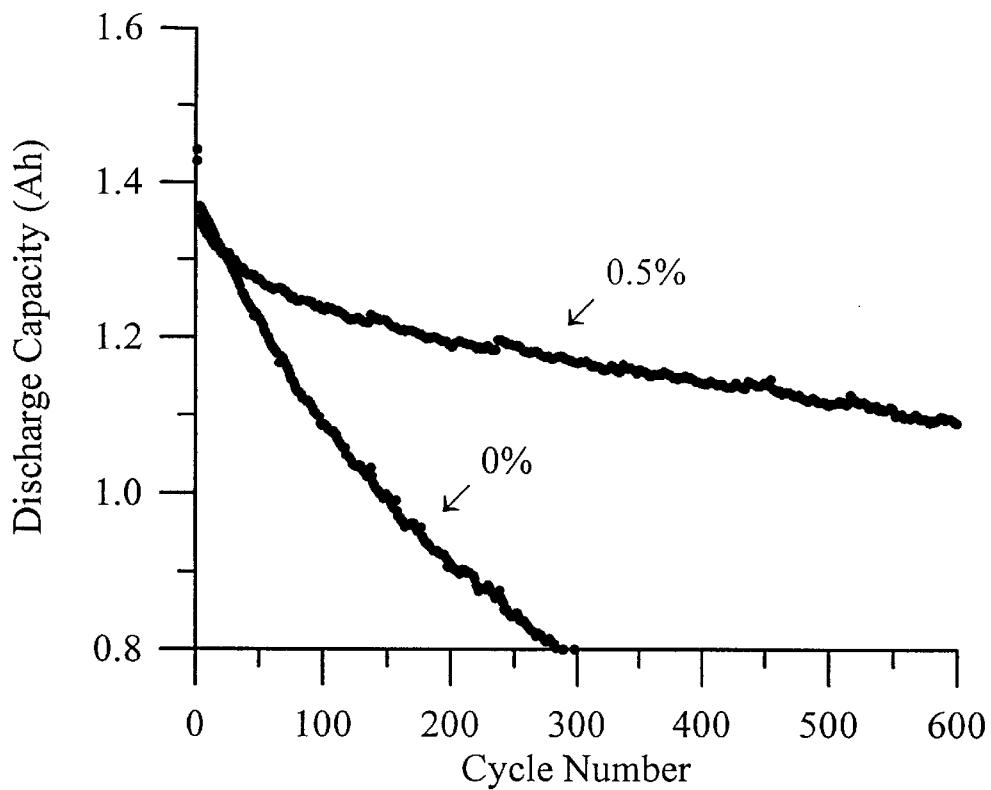
FIG. 5 shows the capacity versus cycle number data for the series of $LiCoO_2$ cathode based 18650 size batteries comprising 0% wt. and 0.5% wt. trimethylboroxin additive in the electrolyte.

Another series of LiCoO$_2$ cathode based 18650 batteries was constructed with varying amounts of the fade reducing additive trimethylboroxin dissolved in the EC/PC/DEC electrolyte prior to assembly. The amounts employed were 0% (control) and 0.5 by weight in the electrolyte. The batteries were then cycled as described above. FIG. 5 shows the capacity versus cycle number data for each battery. The capacity fade rate of the control in this example is significantly worse than that of the similar control in the previous example. This is believed to be due to the use of an inferior grade of LiCoO$_2$ cathode material in this series of batteries. Nonetheless, the capacity fade rate of the battery with the 0.5% wt. trimethylboroxin additive is improved over that of this control battery.

Examples with LiMn$_2$O$_4$ cathode and trimethoxyboroxine additive

Figure 6:
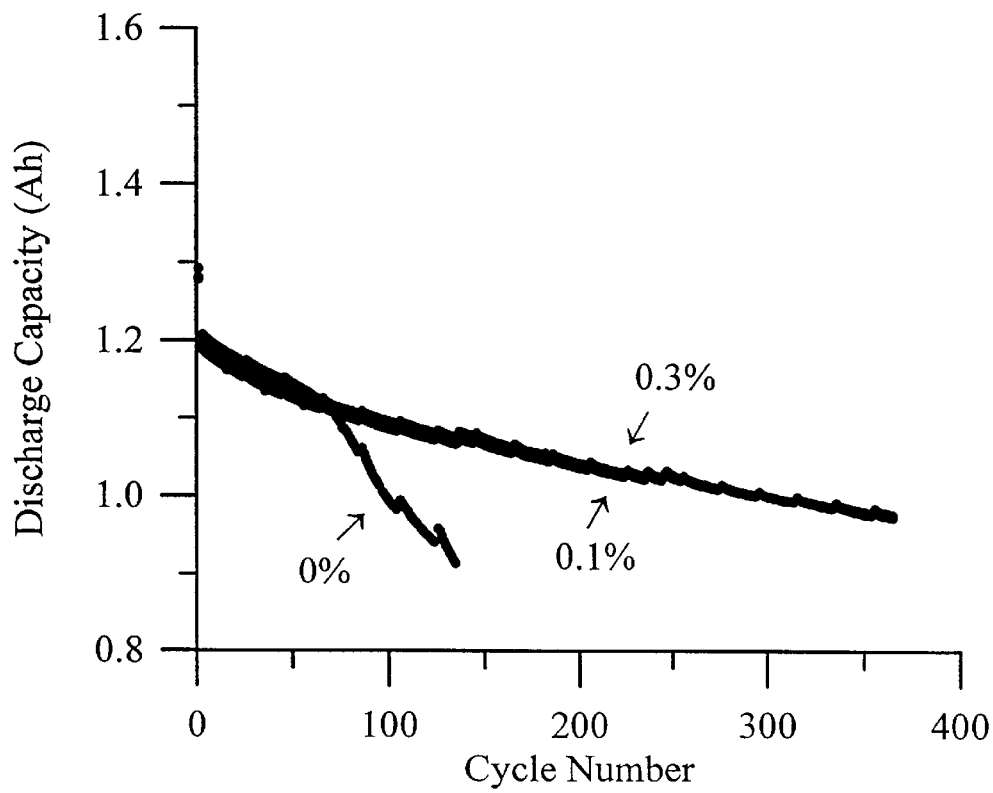
FIG. 6 shows the capacity versus cycle number data for the series of $LiMn_2O_4$ cathode based 18650 size batteries comprising 0% wt., 0.1% wt., and 0.3% wt. trimethoxyboroxine additive in the electrolyte.

A series of Li$_{1.11}$Mn$_2$O$_4$ cathode based 18650 batteries was constructed with varying amounts of the fade reducing additive trimethoxyboroxine dissolved in the EC/PC/EMC electrolyte prior to assembly. The amounts employed were 0% (control), 0.1%, and 0.3% by weight in the electrolyte. The batteries were then cycled as described above. FIG. 6 shows the capacity versus cycle number data for each battery. The batteries with either amount of additive show a similar, much improved capacity fade rate over that of the control.

Examples with LiMn$_2$O$_4$ cathode and trimethylboroxin additive

Figure 7:
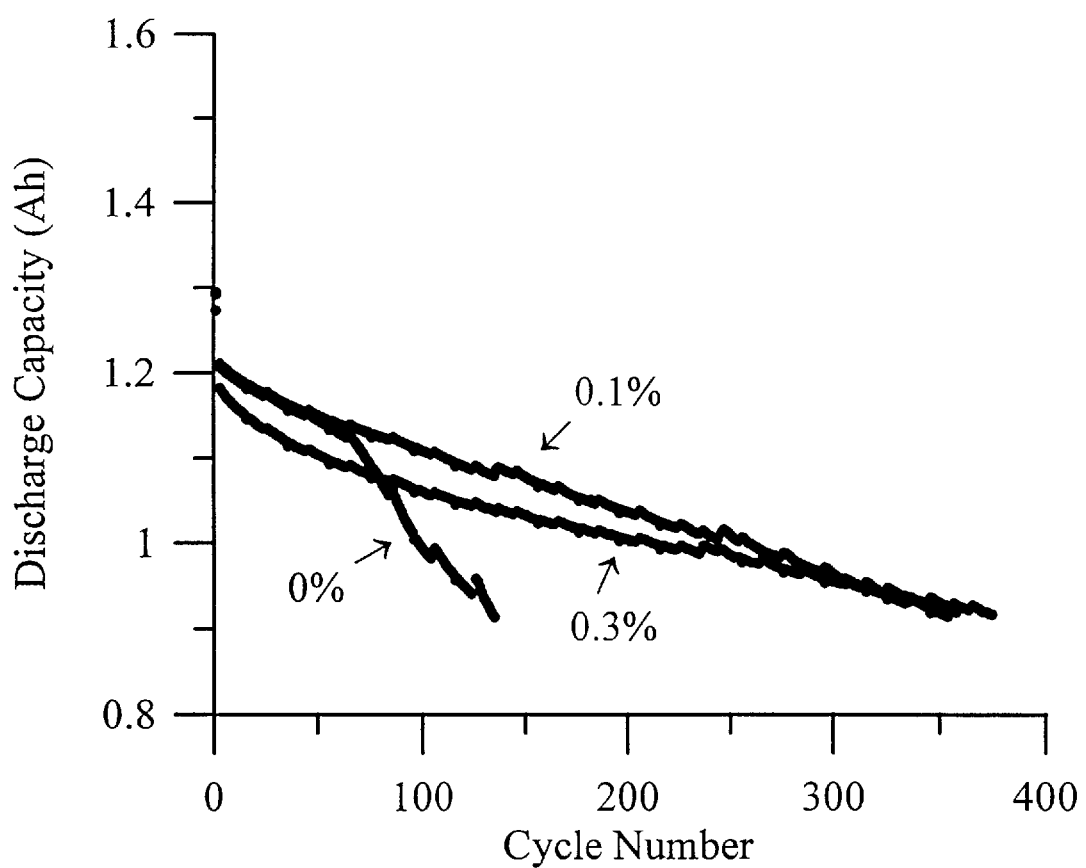
FIG. 7 shows the capacity versus cycle number data for the series of $LiMn_2O_4$ cathode based 18650 size batteries comprising 0% wt., 0.1% wt., and 0.3% wt. trimethylboroxin additive in the electrolyte.

A series of Li$_{1.11}$Mn$_2$O$_4$ cathode based 18650 batteries was constructed with varying amounts of the fade rate reducing additive trimethylboroxin dissolved in the EC/PC/EMC electrolyte prior to assembly. The amounts employed were 0% (control), 0.1%, and 0.3% by weight in the electrolyte. The batteries were then cycled as described above. FIG. 7 shows the capacity versus cycle number data for each battery. The batteries with the additive show an improved capacity fade rate over that of the control. The battery with 0.3% wt. additive has a lower initial capacity but better fade rate than that with the 0.1 wt. additive but the battery with 0.1% wt. additive has a better fade rate reduction than the battery with 0.3% wt. additive. The control battery in this example is the same as that of the preceding example. Thus, it appears that the trimethoxyboroxine additive is somewhat better than the trimethylboroxin additive in this embodiment.

The preceding examples demonstrate that both trimethoxyborine and trimethylboroxin can be effective fade rate reducing additives in lithium ion batteries.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A non-aqueous rechargeable lithium battery having reduced capacity fade rate during cycling, the battery including a lithium insertion compound cathode, a lithium compound anode, a separator, a non-aqueous electrolyte including a lithium salt dissolved in a non-aqueous solvent, and an amount of a fade rate reducing additive compound, comprising boron, oxygen, and organic end groups; the organic end groups being chemically compatible with the cathode, the anode, and the electrolyte; the fade rate reducing additive compound containing at least one boroxine (BO)$_3$ ring.

2. A non-aqueous rechargeable lithium battery as claimed in claim 1 wherein the structure of the fade rate reducing additive compound is denoted by the formula:

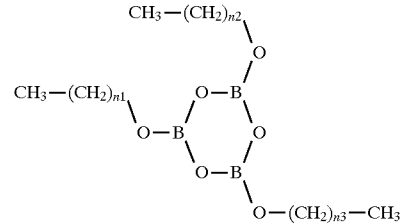

wherein n$_1$, n$_2$, and n$_3$ are integers greater than or equal to zero.

3. A non-aqueous rechargeable lithium battery as claimed in claim 2 wherein the fade rate reducing additive is trimethoxyboroxine.

4. A non-aqueous rechargeable lithium battery as claimed in claim 1 wherein the structure of the fade rate reducing additive compound is denoted by the formula:

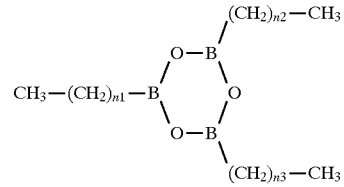

wherein n$_1$, n$_2$, and n$_3$ are integers greater than or equal to zero.

5. A non-aqueous rechargeable lithium battery as claimed in claim 4 wherein the fade rate reducing additive is trimethylboroxin.

6. A non-aqueous rechargeable lithium battery as claimed in claim 1 wherein the amount of the fade rate reducing additive is greater than about 0.1% of the weight of the electrolyte.

7. A non-aqueous rechargeable lithium battery as claimed in claim 1 wherein the amount of the fade rate reducing additive is less than about 2% of the weight of the electrolyte.

8. A non-aqueous rechargeable lithium battery as claimed in claim 1 wherein the fade rate reducing additive is dissolved in the electrolyte.

9. A non-aqueous rechargeable lithium battery as claimed in claim 1 wherein the cathode comprises a lithium transition metal oxide.

10. A non-aqueous rechargeable lithium battery as claimed in claim 9 wherein the lithium transition metal oxide is LiCoO$_2$ or LiMn$_2$O$_4$.

11. A non-aqueous rechargeable lithium battery as claimed in claim 1 wherein the anode comprises a carbonaceous insertion compound.

12. A non-aqueous rechargeable lithium battery as claimed in claim 11 wherein the carbonaceous insertion compound is graphite.

13. A non-aqueous rechargeable lithium battery as claimed in claim 1 wherein the lithium salt is $LiPF_6$.

14. A non-aqueous rechargeable lithium battery as claimed in claim 1 wherein the non-aqueous solvent comprises an organic carbonate.

15. A non-aqueous rechargeable lithium battery as claimed in claim 14 wherein the non-aqueous solvent is a mixture of ethylene carbonate, propylene carbonate, and diethyl carbonate.

16. A non-aqueous rechargeable lithium battery as claimed in claim 14 wherein the non-aqueous solvent is a mixture of ethylene carbonate, propylene carbonate, and ethyl methyl carbonate.

17. A non-aqueous rechargeable lithium battery as claimed in claim 1 wherein the fade rate reducing additive compound is a liquid at ambient temperature.

18. A method of reducing the capacity fade rate during cycling of a non-aqueous rechargeable lithium battery, the battery having a lithium insertion compound cathode, a lithium compound anode, a separator, and a non-aqueous electrolyte including a lithium salt dissolved in a non-aqueous solvent, which comprises incorporating into the battery an amount of a fade rate reducing additive compound comprising boron, oxygen, and organic end groups; the organic end groups being chemically compatible with the cathode, the anode, and the electrolyte; and the structure of the fade rate reducing additive containing at least one $(BO)_3$ boroxine ring.

19. A method as claimed in claim 18 wherein the fade rate reducing additive is trimethoxyboroxine or trimethylboroxin.

20. A method as claimed in claim 18 wherein the amount of the fade rate reducing additive compound is greater than about 0.5% of the weight of the electrolyte.

21. A method as claimed in claim 18 wherein the amount of the fade rate reducing additive compound is sufficiently small that the thermal stability threshold of the battery remains essentially unchanged.

22. A method as claimed in claim 21 wherein the amount of the fade rate reducing additive compound is less than about 2% of the weight of the electrolyte.

23. A method as claimed in claim 18 wherein the fade rate reducing additive compound is dissolved in the electrolyte.

24. A method use as claimed in claim 18 wherein the structure of the fade rate reducing additive compound is:

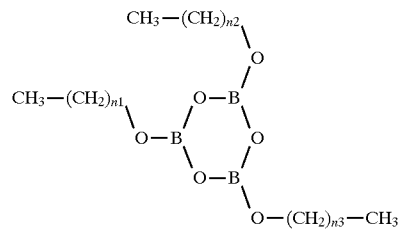

wherein $n_1$, $n_2$, and $n_3$ are integers greater than or equal to zero.

25. A method use as claimed in claim 18 wherein the structure of the fade rate reducing additive compound is:

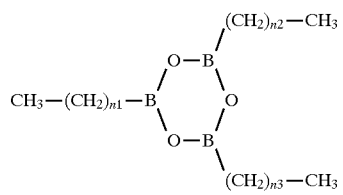

wherein $n_1$, $n_2$ and $n_3$ are integers greater than or equal to zero.

* * * * *

UNITED STATES PATENT AND TRADEMARK OFFICE
CERTIFICATE OF CORRECTION

PATENT NO. : 5,891,592
DATED : April 6, 1999
INVENTOR(S) : Mao et al.

It is certified that error appears in the above-identified patent and that said Letters Patent is hereby corrected as shown below:

Column 12, line 8, delete "use".
Column 12, line 23, delete "use".

Signed and Sealed this

Twelfth Day of October, 1999

Attest:

Q. TODD DICKINSON

Attesting Officer     Acting Commissioner of Patents and Trademarks